United States Patent [19]

Tsumita et al.

[11] 3,943,119

[45] Mar. 9, 1976

[54] TUBERCULIN ACTIVE PROTEINS AND PEPTIDES FROM THE CELLS OF TUBERCLE BACILLI

[75] Inventors: Toru Tsumita; Seishi Kuwabara, both of Tokyo, Japan

[73] Assignee: Mitsui Pharmaceuticals, Incorporated, Tokyo, Japan

[22] Filed: Mar. 28, 1974

[21] Appl. No.: 455,798

Related U.S. Application Data

[63] Continuation-in-part of Ser. No. 374,663, June 28, 1973, Pat. No. 3,888,837.

[52] U.S. Cl.............. 260/112.5 R; 195/29; 424/9; 424/177
[51] Int. Cl.² C07C 103/52; C08H 1/00; C12B 1/00
[58] Field of Search.............................. 260/112.5

[56] References Cited
OTHER PUBLICATIONS

Kotani et al., Chem. Abstr., 75:31580s (1971).

Trufanov et al., Chem. Abstr., 75:137733j (1971).

Degtyarenko et al., Chem. Abstr., 69:65770v (1968).

Degtyarenko et al., Chem. Abstr. 69:83432r (1968).

*Primary Examiner*—Lewis Gotts
*Assistant Examiner*—Reginald J. Suyat
*Attorney, Agent, or Firm*—Fisher, Christen & Sabol

[57] ABSTRACT

Tuberculin active simple proteins and peptides which have the following peptide linkage —Asn—Gly—Ser—Gln—Met— as a tuberculin active functional group, and a process for preparing the same from the cells of tubercle bacilli.

**3 Claims, No Draw

TUBERCULIN ACTIVE PROTEINS AND PEPTIDES FROM THE CELLS OF TUBERCLE BACILLI

This application is a continuation-in-part of co-pending application Ser. No. 374,663 filed June 28, 1973, now U.S. Pat. No. 3,888,837.

The present invention is concerned with tuberculin active simple proteins and peptides which have the following peptide linkage.

—Asn—Gly—Ser—Gln—Met— as a tuberculin active functional group.

It is well known that purified protein derivative(PPD) from extracellular old tuberculin(OT) has been used exclusively for the diagnosis of tuberculosis. Unfortunately, in addition to tuberculin active proteins, PPD contains other inactive proteins, nucleic acids, polysaccharides and fatty acids. As tuberculin active simple proteins have not been obtained, their physicochemical, chemical and biological properties have not been determined.

The present inventors have succeeded in isolating tuberculin active simple proteins from the cells of tubercle bacilli and have obtained them as crystalline forms. Subsequently the amino acid sequences and amino acid compositions per molecule of the obtained proteins have been determined. Besides, they have obtained tuberculin active peptides by hydrolyzing the above obtained proteins and fractionating the resultant hydrolysates. From the results of the investigation, it has been found that the tuberculin activity is closely connected with the afore-said tuberculin active functional group in proteins and peptides.

The tuberculin active simple proteins of the present invention are prepared from the cells of tubercle bacilli by treating the above bacillary cells with organic solvents, digesting the resultant materials with nucleases, dialyzing the obtained water-soluble proteins and fractionating the resultant dialysates by chromatography and/or gel filtration.

The tubercle bacilli used in the present invention are human- or bovine-type tubercle bacilli including Bacille de Calmette et Guerin(BCG) and others. The obtainable tuberculin active simple proteins depend upon the tubercle bacilli and preparation conditions used in the present method. For instance, the tuberculin active simple protein from human-type *Mycobacterium tuberculosis* strain Aoyama B is composed of 89 amino acid residues per molecule. On the other hand, the tuberculin active simple protein from BCG is composed of 135 amino acid residues per molecule.

Tubercle bacilli are treated with organic solvents such as ketones, alcohols, carboxylic acids, and the like. Acetone, methanol or acetic acid is preferably employed. These solvents may, of course, be used with water. The solvent-treated materials are digested with nucleases such as ribonucleases, deoxyribonucleases, and the like. The water-soluble proteins are separated from the resultant mixtures and dialyzed against buffers of pH 5.5 – 7.8 such as tris(hydroxymethyl)aminomethane—hydrochloric acid buffer of pH 7.0 containing ethylenediamine tetraacetic acid, dibasic sodium phosphate—monobasic potassium phosphate buffer of pH 7.2 containing ethylenediamine tetraacetic acid, and the like.

The dialyzed tuberculin active proteins are fractionated by chromatography and/or gel filtration. Especially, column chromatography using ion-exchange cellulose or gel filtration using bridged dextran polymer is preferably employed. The ion-exchange celluloses which may be employed to fractionate the above dialysates may be, for example, aminoethyl(AE)-cellulose, diethylaminoethyl(DEAE)-cellulose, triethylaminoethyl(TEAE)-cellulose or epichlorohydrin-triethanolamine(ECTEOLA)-cellulose. The bridged dextran polymers which may be employed to fractionate the above dialysates may be, for example, Sephadex-(trade name of Pharmacia Co.)G series(G-20 G-200) or ion-exchange Sephadex such as carboxymethyl(CM)-Sephadex, sulfoethyl(SE)-Sephadex, and the like. The dialysed proteins are eluted with the afore-said buffers.

The tuberculin active simple proteins of the present invention are soluble in water and their molecular weights 5,000 – 25,000 are depending upon the tubercle bacilli used for preparing them and the preparation conditions thereof. The tuberculin skin tests indicate that the tuberculin active simple proteins of the present invention have tuberculin activities 10 – 100 times potent than that of PPD against guinea pigs sensitized with heat-killed *Mycobacterium tuberculosis* strain Aoyama B.

The tuberculin active peptides of the present invention are prepared by hydrolyzing the above-mentioned tuberculin proteins and are obtained by fractionating the resultant hydrolysates by chromatography and/or gel filtration. The tuberculin active proteins are hydrolyzed chemically or enzymatically. The chemical hydrolysis is carried out with a mineral acid. The enzymatic hydrolysis is carried out with a proteolytic enzyme such as prypsin, chymotrypsin, pepsin, bacterial proteinases, carboxypeptidase A or B, and the like. The resultant hydrolysates are fractionated by column chromatography, paper chromatography, paper electrophoresis, gel filtration, and the like. The gel filtration is carried out by eluting with an ammonium acetate buffer of pH 5.9 through Sephadex G-25 or CM-Sephadex, with a pyridine acetate buffer of pH 4.5 through SE-Sephadex C-50 or with a pyridine acetate buffer of pH 3.1 through Dowex 50-X2 or 1-X2.

The tuberculin active peptides of the present invention are white crystalline solids, soluble in water and about 500 – 1,500 in the molecular weights. The tuberculin skin tests indicate that the tuberculin active peptides of the present invention have tuberculin activities comparable to or more potent than that of PPD against guinea pigs sensitized with heat-killed *Mycobacterium tuberculosis* strain Aoyama B or BCG.

The following examples illustrate the preparation and isolation of the tuberculin active simple proteins and peptides of the present invention.

EXAMPLE 1

The cultured bacillary cells(100g) of Mycobacterium tuberculosis strain Aoyama B were killed by heating at 120°C for 30 minutes. The cells were separated from the culture medium by filtration, then sonically disrupted and treated with acetone. The resultant material was digested with ribonuclease and deoxyribonuclease and the digested mixture was centrifuged to separate water-soluble proteins. The water-soluble proteins thus obtained were dialyzed against 0.001M tris(hydroxymethyl)aminomethane—hydrochloric acid buffer of pH 7.0 containing 0.0001M ethylenediamine tetraacetic acid.

The resultant dialysate was chromatographed on DEAE-cellulose column. The elution was carried out in a sodium chloride gradient. Virtually all of the tuberculin activity was found in the second protein fraction. Further chromatography on Sephadex G-200 was carried out in the same buffer as before and fractionated into three fractions. Nearly all of the tuberculin active material was found in the major proteins fraction. The active material crystallized spontaneounly when the solution was kept at 4°C in the mixed solution of the same buffer with purified acetone. From 100g of the bacillary cells, 25mg of tuberculin active simple protein was obtained.

The tuberculin active simple protein thus obtained was composed of 89 amino acid residues and its amino acid sequence and amino acid composition per molecule were determined as follows.

```
    Amino acid sequence
    1   2   3   4   5   6   7   8   9  10  11  12  13
H₂N-Arg-Leu-Leu-Asp-Asp-Thr-Pro-Glu-Vel-Lys-Val-Leu-Gly-
   20  21  22  23  24  25  26  27  28 29  30
   -Glu-Thr-Pro-Lys-Ala-Glu-Pro-Cys-Ile-Asp-Leu-
   50  51  52  53  54  55  56 57  58 59  60
   -Tyr-Ala-Glu-Val-Thr-Phe-His-Glu-Ile-Cys-Arg-
   70  71  72  73  74         85  86  87  88  89
   -Asn-Gly-Ser-Gln-Met-     -Ala-Thr-Val-Ala-Lys-COOH
(Asn and Gln represent asparagine residue and glutamine
residue, respectively. Other abbreviations represent the
usual meanings. Cysteine residues at the position
27 and 59 form one intrachain disulfide bridge.)
        Amino acid composition per molecule
Lys 4, His 1, Arg 4, Cys 2, Asp 11(containing one asparagine
residue), Thr 5, Ser 4, Glu 11(containing one glutamine
residue), Pro 5, Gly 7, Ala 11, Val 8, Met 1, Ile 4,
Leu 7, Try 2 and Phe 2.
```

Tuberculin skin test showed that the obtained tuberculin active simple protein had a tuberculin activity 100 times potent than that of PPD against guinea pigs sensitized with heat-killed *Mycobacterium tuberculosis* strain Aoyama B or BCG.

EXAMPLE 2

The tuberculin active simple protein composed of 135 amino acid residues was also prepared from BCG by the same method as in Example 1. The amino acid sequence and amino acid composition per molecule of this protein were determined and found to be similar to those of the tuberculin active protein in Example 1.

Tuberculin skin test indicated that this tuberculin active protein has a tuberculin activity nearly equal to that of the tuberculin active protein in Example 1 against guinea pigs sensitized with heat-killed *Mycobacteriun tuberculosis* strain Aoyama B or BCG.

EXAMPLE 3

The tuberculin active simple protein obtained in Example 1 was enzymatically hydrolyzed at 37°C for 6 hours in the 1% trypsin solution of pH 8.4. Two dimensional high level voltage paper electrophoresis of the resultant hydrolysate on Whatman paper was carried out at 75V/cm in pyridine acetate buffer of pH 4.5 and followed by paper chromatography which was carried out in the butanol-acetic acid-water (4:1:4, by volume) mixture.

The above development resulted in the separation of several tuberculin active peptides. One of them was a pentapeptide which has the following amino acid sequence.

```
       1   2   3   4   5
H₂N-Asn-Gly-Ser-Gln-Met-COOH
```

Another was a nonapeptide which has the molecular weight of about 950.

Tuberculin skin tests showed that these tuberculin active peptides had 1 – 10% activities of the starting tuberculin protein.

EXAMPLE 4

The tuberculin active protein obtained in Example 1 was hydrolyzed in the 0.5% chymotrypsin solution. The resultant hydrolysate was chromatographed on Sephadex G-25 column, elution being carried out with an ammonium acetate buffer of pH 5.9. The tuberculin active peptides thus obtained were further fractionated with pyridine acetate buffer of pH 3.1 on Dowex 1-X2 column. The tuberculin active pentapeptide thus obtained was the same as in Example 3.

EXAMPLE 5

The tuberculin active simple protein in Example 2 was treated in the same way as in Example 3. And the same tuberculin active pentapeptide as in Example 3 was also obtained.

What is claimed is:

1. A tuberculin active simple protein from Mycobacterium tuberculosis strain Aoyama B which is characterized by the following amino acid sequence:

```
       1   2   3   4   5   6   7   8   9  10  11  12  13   20
H₂N-Arg-Leu-Leu-Asp-Asp-Thr-Pro-Glu-Val-Lys-Val-Leu-Gly- -Glu-
    21  22  23  24  25  26  27 28  29  30      50  51  52  53
    Thr-Pro-Lys-Ala-Glu-Pro-Cys-Ile-Asp-Leu- -Tyr-Ala-Glu-Val-
    54  55   56  57 58  59  60      70  71  72  73  74   85
    Thr-Phe-His-Glu-Ile-Cys-Arg- -Asn-Gly-Ser-Gln-Met- -Ala-
    86  87  88  89
    Thr-Val-Ala-Lys-COOH
``` wherein Asn and Gln represent asparagine residue and glutamine residue, respectively, and the remaining abbreviations represent the usual meanings and wherein the cysteine residues at positions 27 and 59 form one intra-chain disulfide bridge, said protein also being characterized by the following amino acid composition per molecule:

Lys 4, His 1, Arg. 4, Cys 2, Asp 11 (containing one asparagine residue), Thr 5, Ser 4, Glu 11 (containing one glutamine residue), Pro 5, Gly 7, Ala 11, Val 8, Met 1, Ile 4, Leu 7, Tyr 2 and Phe 2.

2. A tuberculin active fragment which is prepared by enzymatic digestion of the tuberculin active simple protein of claim 1 and which has the following tuberculin active group therein:

-Asn-Gly-Ser-Gln-Met-.

3. A tuberculin active pentapeptide whose amino acid sequence is as follows.

```
       1   2   3   4   5
H₂N-Asn-Gly-Ser-Gln-Met-COOH
```

* * * * *